United States Patent
Brown et al.

(10) Patent No.: US 11,324,401 B1
(45) Date of Patent: May 10, 2022

(54) COMPUTING SYSTEM FOR WOUND TRACKING

(71) Applicant: Allscripts Software, LLC, Raleigh, NC (US)

(72) Inventors: Joshua Brown, Cary, NC (US); David Windell, Raleigh, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 151 days.

(21) Appl. No.: 16/561,277

(22) Filed: Sep. 5, 2019

(51) Int. Cl.
*A61B 5/00* (2006.01)
*G16H 30/40* (2018.01)
*G16H 80/00* (2018.01)
*G16H 10/60* (2018.01)
*G06T 7/00* (2017.01)

(52) U.S. Cl.
CPC .......... *A61B 5/0077* (2013.01); *A61B 5/445* (2013.01); *G16H 10/60* (2018.01); *G16H 30/40* (2018.01); *G16H 80/00* (2018.01); *G06T 7/0012* (2013.01); *G06T 2207/30088* (2013.01)

(58) Field of Classification Search
CPC ...... A61B 5/0077; A61B 5/445; G16H 10/60; G16H 80/00; G16H 30/40; G06T 2207/30088; G06T 7/0012
See application file for complete search history.

(56) References Cited

U.S. PATENT DOCUMENTS

| | | | |
|---|---|---|---|
| 8,213,695 B2 | 7/2012 | Zouridakis et al. | |
| 9,042,967 B2 | 5/2015 | Dacosta et al. | |
| 9,286,537 B2 | 3/2016 | Radha Krishna Rao et al. | |
| 9,501,624 B2 | 11/2016 | Vishnubhatla et al. | |
| 2008/0260218 A1* | 10/2008 | Smith | A61B 5/444 382/128 |
| 2015/0150457 A1 | 6/2015 | Wu et al. | |
| 2016/0228049 A1* | 8/2016 | Nackaerts | G16H 40/67 |
| 2016/0259992 A1* | 9/2016 | Knodt | H04N 5/232941 |
| 2017/0104925 A1* | 4/2017 | Ng | H04N 5/247 |
| 2018/0046758 A1* | 2/2018 | Gogin | G16H 50/20 |
| 2018/0189447 A1* | 7/2018 | Khatri | G16H 30/40 |
| 2020/0121245 A1* | 4/2020 | Barclay | A61B 5/445 |
| 2020/0211693 A1* | 7/2020 | Adiri | G06Q 40/08 |

* cited by examiner

*Primary Examiner* — Chan S Park
*Assistant Examiner* — Daniel C Chang
(74) *Attorney, Agent, or Firm* — Calfee, Halter & Griswold LLP

(57) ABSTRACT

A computing system for wound tracking is disclosed herein. A server computing device receives a first image of a wound of a patient captured by a first camera. Subsequently, the server computing device receives a message generated by a computing device, the message indicating that a second camera of the computing device is to capture a second image of the wound. Responsive to receiving the message, the server computing device causes data to be transmitted to the computing device, the data based in part upon the first image. The data causes the computing device to present a semi-transparent overlay to a view of the wound on a display as perceived through a lens of the second camera, the semi-transparent overlay indicative of the first image. The computing device captures the second image via the second camera and causes the second image to be received by the server computing device.

18 Claims, 8 Drawing Sheets

COMPUTING SYSTEM FOR WOUND TRACKING

BACKGROUND

Electronic health records applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

A conventional EHR is often configured with wound tracking functionality, wherein images of a wound of a patient taken over a period of time may be stored as part of patient records for the patient. The EHR may present the images of the wound on a display, and a healthcare worker may inspect the images of the wound in order to make decisions with respect to treating the wound. For instance, if one or more images of the wound indicate to the healthcare worker that the wound is infected, the healthcare worker may prescribe antibiotics to the patient.

In a conventional wound tracking scenario, when a patient is visiting a healthcare worker (e.g., a primary care provider) for treatment for a wound, a first computing device executing an EHR captures a first image of the wound via a first camera and stores the first image of the wound in a data store. Sometime thereafter, the patient may wish to send a second image of the wound to the healthcare worker in order to apprise the healthcare worker as to whether the wound is healing properly. A second computing device operated by the patient captures the second image of the wound via a second camera and emails the second image to an email account associated with the healthcare worker. The first computing device operated by the healthcare worker may then receive input from the healthcare worker that causes the first computing device to download the second image of the wound from the email account and store the second image in the data store. The EHR may display the first image of the wound and the second image of the wound on a display to enable the healthcare worker to ascertain whether the wound is healing properly and whether the patient requires further treatment.

Conventional EHRs suffer from various deficiencies with respect to wound tracking for patients. First, conventional EHRs cannot receive an image of a wound of a patient directly from a computing device operated by the patient. As noted above, a computing device operated by a healthcare worker must receive manual input from the healthcare worker in order for the image to be stored in a data store accessible to the EHR, which is an inefficient use of computing resources of the computing device operated by the healthcare worker.

Second, parameters (e.g., image resolution, flash intensity, etc.) of cameras that captures the images of the wound may vary, and hence it may be difficult to capture consistent images of the wound, which may make tracking healing progress of the wound difficult for the healthcare worker and/or the patient. For instance, a first image of the wound may be captured by a first camera with a relatively bright flash, whereas a second image of the wound may be captured by a second camera with a relatively dim flash.

Third, the cameras of the computing devices may be oriented differently when capturing images of the wound, thus adding further difficulty to tracking the healing progress of the wound. For instance, the first camera may capture the first image of the wound when the first camera is located a first distance from the wound and the second camera may capture the second image of the wound when the second camera is located at a second distance from the wound. If the second distance is greater than the first distance, the wound may appear larger in the second image than in the first image, even if the wound has in fact shrunk.

Moreover, lighting conditions of environments in which images of the wound are captured may also vary, thus making comparisons between the images difficult. For instance, the first image of the wound may be captured in a room with bright lighting conditions, whereas the second image of the wound may be captured in a room with dim lighting conditions.

SUMMARY

The following is a brief summary of subject matter that is described in greater detail herein. This summary is not intended to be limiting as to the scope of the claims.

Disclosed herein are various technologies pertaining to tracking wounds of patients. With more specificity, an electronic health records application (EHR) is described herein, wherein the EHR is a distributed application that has both client-side functionality (client EHR) and server-side functionality (server EHR). A patient portal application is also described herein, wherein the patient portal application is also a distributed application that has both client-side functionality (client patient portal application) and server-side functionality (server patient portal application). The EHR and the patient portal application communicate with one another in order to facilitate tracking wounds of patients via images of the wounds captured by cameras of computing devices operated by healthcare workers and/or patients.

In operation, a server computing device executing a server EHR receives a first image of a wound of a patient that been captured by a first camera. The first camera may be comprised by a first computing device. The server computing device may also receive camera data that is indicative of parameters of the first camera (e.g., image resolution, color characteristics, etc.) from the first computing device. In an example, the first computing device may be operated by a healthcare worker that is providing treatment to the patient for the wound. Hence, the first computing device may execute a client EHR. The server computing device stores the first image of the wound in a data store that is accessible to the server computing device. The server computing device may also store the camera data for the first camera in association with the first image of the wound.

Subsequently, the server computing device receives a message generated by a second computing device. The message comprises an indication that the second computing device is to capture a second image of the wound of the patient by way of a second camera comprised by the second computing device. The second camera may have different parameters than the parameters of the first camera. In an example, the second computing device may be operated by the patient. Hence, the second computing device may execute a client patient portal application and the client patient portal application may transmit the message to a server patient portal application executing on a second server computing device. The second server computing device may then transmit the message to the server computing device.

Responsive to receiving the message, the server computing device retrieves the first image of the wound from the data store and generates data based at least in part upon the first image. The server computing device may also retrieve the camera data for the first camera from the data store and generate the data based additionally upon the camera data for the first camera. The server computing device causes the data to be transmitted to the second computing device. The data causes the second computing device to present a semi-transparent overlay on a display of the second computing device. The semi-transparent overlay is indicative of the first image of the wound and is overlaid upon a view of the wound shown on the display as perceived through a lens of the second camera. The data may also cause the second computing device to adjust parameters of the second camera to match the parameters of the first camera in order to ensure consistency between the first image and the second image. Moreover, the data may cause the second computing device to present instructions on the display, the instructions indicating a direction in which an operator of the second computing device is to move the second computing device (and hence the second camera) in order for the second camera to capture the second image under similar conditions as the first image.

The second computing device captures the second image of the wound by way of the second camera when the second camera is positioned with respect to the wound such that at least a portion of the semi-transparent overlay is positioned over the wound shown on the display. The second computing device causes the second image of the wound to be received by the server computing device, whereupon the server computing device stores the second image of the wound in the data store. Subsequently, the server computing device may cause the first image of the wound and the second image of the wound to be presented on a display of the first computing device and/or the display of the second computing device. Additionally, the server computing device may determine whether the wound is infected based upon at least one of the first image or the second image. When the wound is infected, the server computing device may generate and transmit an alert to the first computing device and/or the second computing device, the alert indicating that the wound is infected.

The above-described technologies present various advantages over conventional EHRs. First, unlike conventional technologies, the above-described technologies enable a computing device operated by a patient to cause images of a wound of the patient to be received by an EHR without having to resort to email and manual download into a data store, which results in reduced use of computing resources. Second, through use of the camera data, the above-described technologies ensure that images of a wound captured by cameras with disparate parameters are captured under consistent conditions (e.g., consistent lighting conditions) that facilitate comparison between the images of the wound. Third, the above-described technologies ensure that the images of the wound are captured from similar perspectives (e.g., the cameras are a similar distance from the wound when the cameras capture the images of the wound), which also facilitates comparison between the images of the wound.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
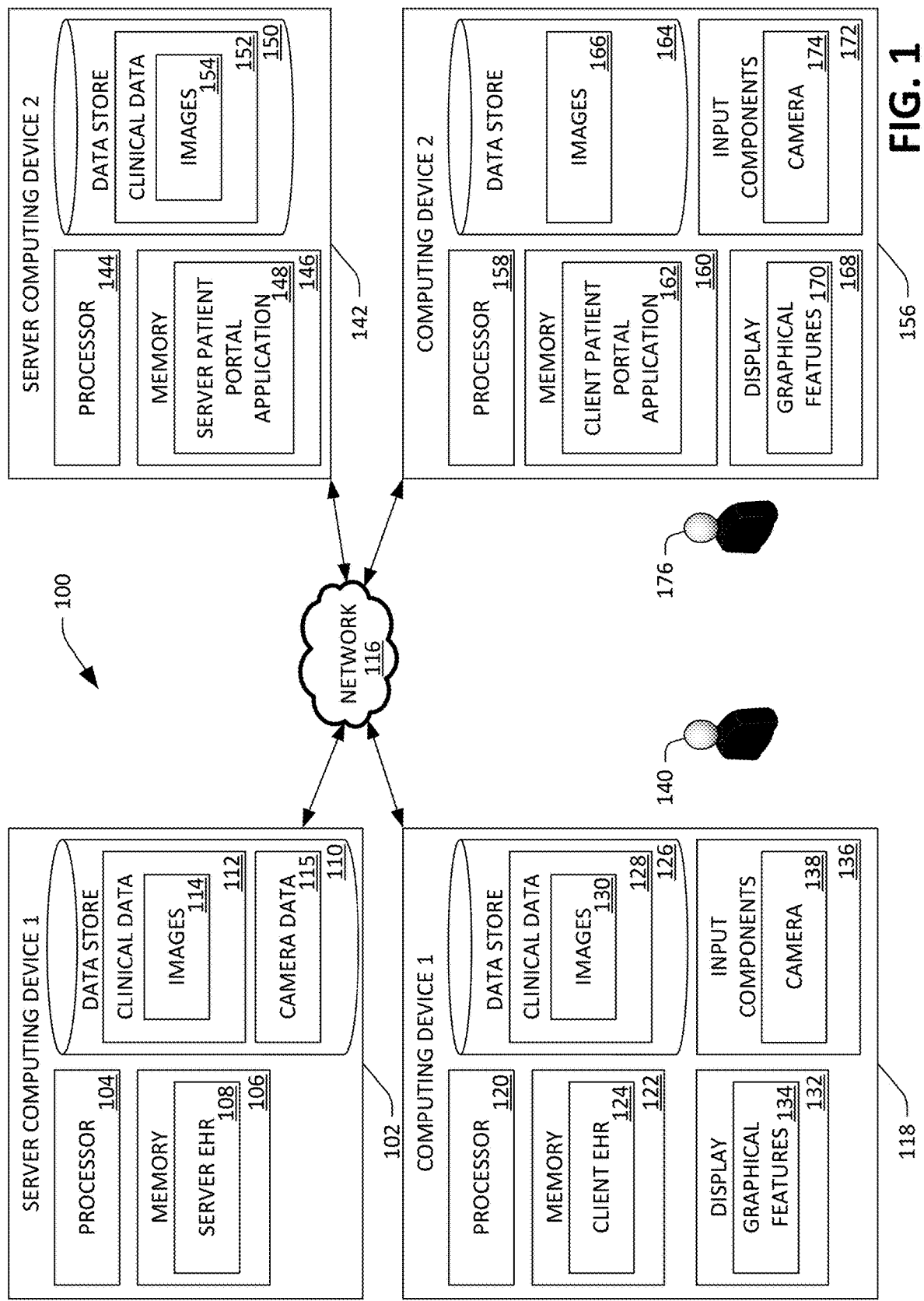
FIG. 1 is a functional block diagram of an exemplary computing system that facilitates wound tracking for patients.

Various technologies pertaining to wound tracking via images of wounds of patients are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "application," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

As used herein, the term "wound" refers to an injury in which skin of a patient is torn, cut, or punctured (an "open wound") or where a blunt force trauma causes a contusion (a "closed wound") of the skin. Open wounds may include, but are not limited to, incision wounds, lacerations, abrasions, avulsions, puncture wounds, penetration wounds, and/or gunshot wounds. Closed wounds may include, but are not limited to, hematomas and/or crush injuries.

With reference to FIG. 1, an exemplary computing system 100 that facilitates wound tracking for patients is illustrated. The computing system 100 includes a first server computing device 102. The first server computing device 102 comprises a processor 104 and memory 106, wherein the memory 106 has a server electronic health records application (server EHR) 108 loaded therein. In general, the server EHR 108 (when executed by the processor 104) is configured to perform a variety of tasks related to patient healthcare in a healthcare facility (e.g., patient intake, prescription generation, patient record creation and maintenance, etc.).

The first server computing device 102 further includes a data store 110. The data store 110 comprises clinical data 112 for patients, wherein the server EHR 108 maintains the clinical data 112 for the patients. The clinical data 112 may include electronic health records, prescription records, claims data, patient/disease registries, health surveys data, clinical trials data, etc. As will be described in greater detail below, the clinical data 112 includes images 114 of wounds of patients. Alternatively, the images 114 may be stored separately from the clinical data 112 for the patients. The images 114 are stored in a suitable computer-readable image format, such as in a Portable Network Graphic (PNG) format, a Joint Photographic Experts Group (JPEG) format, a bitmap image file format (BMP), etc. The images 114 of the wounds may comprise images of wounds that are labeled with identifiers for patients to which the wounds belong, as well as de-identified images of wounds that have been stripped of the identifiers for the patients.

The data store 110 may also comprise camera data 115 for cameras that capture the images 114 of the wounds of the patients. The camera data 115 is indicative of parameters of the cameras when the cameras capture the images 114 of the wounds. For instance, the parameters may include image resolutions of the cameras when the cameras capture the images 114, durations of flashes generated by the cameras when the cameras capture the images 114, intensities of the flashes generated by the cameras when the cameras captures the images 114, zoom levels of the cameras when the camera capture the images 114, and/or color characteristics (e.g., color temperature, white balance, etc.) of the cameras when the cameras capture the images 114.

The computing system 100 further includes a first computing device 118 that is in communication with the first server computing device 102 by way of a network 116 (e.g., the Internet, intranet, etc.). The first computing device 118 is operated by a healthcare worker 140 (e.g., a clinician, a nurse, etc.) in a healthcare facility. In an example, the first computing device 118 may be a mobile computing device, such as a tablet computing device or a smartphone. The first computing device 118 comprises a processor 120 and memory 122, wherein the memory 122 has a client electronic health records application (client EHR) 124 loaded therein. The client EHR 124 (when executed by the processor 120) is configured to communicate with the server EHR 108 in order to perform tasks related to patients in the healthcare facility.

The first computing device 118 may include a data store 126. The data store 126 may store clinical data 128 for patients, wherein the clinical data 128 is a subset of the clinical data 112 stored in the data store 110. As such, the clinical data 128 may include images 130 of wounds of patients, wherein the images 130 are a subset of the images 114.

The first computing device 118 includes a display 132, whereupon graphical features 134 may be presented thereon. For instance, the graphical features 134 may include some or all of the images 130, graphical user interfaces (GUIs) that may be overlaid with the images 130 prior to and concurrently with capturing the images 130, etc. In an embodiment, the display 132 may be a touchscreen display.

Additionally, the first computing device 118 includes input components 136 that enable the first computing device 118 to receive input. The input components 136 include a camera 138 (or several cameras) that is configured to captures images of surroundings of the camera 138 (e.g., images of wounds of patients). Although the camera 138 is depicted in FIG. 1 as being part of the first computing device 118, it is to be understood that the camera 138 may be external to the first computing device 118. For instance, the camera 138 may be a standalone camera that is in wired or wireless communication with the first computing device 118. The input components 136 may also include a mouse, a keyboard, a touchscreen, a trackpad, a scroll wheel, a microphone, a video camera, etc.

The computing system 100 additionally includes a second server computing device 142 that is in communication with the first server computing device 102 and computing devices operated by patients by way of the network 116 (or another network). The second server computing device 142 may also be in communication with the first computing device 118 by way of the network 116 (or another network). The second server computing device 142 comprises a processor 144 and memory 146, wherein the memory 146 has a server patient portal application 148 loaded therein. In general, the server patient portal application 148 is configured to communicate with the server EHR 108 and the computing devices operated by the patients in order to enable the patients to access their clinical data (or portions thereof), including prescription medications, health records, communications with healthcare providers, etc. The server patient portal application 148 is also configured to enable the patients to upload data (e.g., images of wounds) that can be included in clinical data of the patients.

The second server computing device 142 may include a data store 150. The data store 150 stores clinical data 152 for patients, wherein the clinical data 152 may be a subset of the clinical data 112 maintained by the server EHR 108. The clinical data 152 includes images 154 of wounds of patients that are received from the computing devices operated by the patients. The images 154 may also include images received from computing devices operated by healthcare workers (e.g., the first computing device 118).

The computing system 100 also includes a second computing device 156 that is in communication with the second server computing device 142 by way of the network 116 (or another network). The second computing device 156 is operated by a patient 176 that receives, has received, or will receive treatment for a wound at a healthcare facility that utilizes the server EHR 108. Alternatively, the second computing device 156 may be operated by an associate of the patient 176 (e.g., a family member). In an example, the second computing device 156 may be a mobile computing device, such as a tablet computing device or a smartphone. The second computing device 156 comprises a processor 158 and memory 160, wherein the memory 160 has a client patient portal application 162 loaded therein. The client patient portal application 162 (when executed by the processor 158) is configured to communicate with the server patient portal application 148 in order to enable the patient 176 to access his or her clinical data and/or enable the patient 176 to upload self-reported health data (including images of wounds of the patient 176) to the server patient portal application 148.

The second computing device 156 may include a data store 164. The data store 164 may store images 166 of wounds of the patient 176 that are captured by way of a camera comprised by the second computing device 156. The second computing device 156 includes a display 168, whereupon graphical features 170 may be presented thereon. For instance, the graphical features 170 may include some or all of the images 166, GUIs that may be overlaid with the images 166 prior to and concurrently with capturing the images 166, etc. In an embodiment, the display 168 may be a touchscreen display.

Additionally, the second computing device 156 includes input components 172 that enable the second computing device 156 to receive input. The input components 172 include a camera 174 (or several cameras) that are configured to captures images of surroundings of the camera 174 (e.g., the images 166 of the wounds of the patient 176). Although the camera 174 is depicted in FIG. 1 as being a part of the second computing device 156, it is to be understood that the camera 174 may be external to the second computing device 156. The input components 172 may also include a mouse, a keyboard, a touchscreen, a trackpad, a scroll wheel, a microphone, a video camera, etc.

Operation of the computing system 100 is now set forth. It is contemplated that the patient 176 has a wound (e.g., an incision, a laceration, etc.) on his/her skin and that the healthcare worker 140 is providing treatment to the patient 176 for the wound in a healthcare facility. The server EHR 108 receives a first image of the wound captured by the camera 138. More specifically, the client EHR 124 may receive input from the healthcare worker 140 that causes the camera 138 to capture the first image of the wound. In an embodiment, the client EHR 124 may autodetect edges of the wound of the patient 176 and present instructions to the healthcare worker 140 on the display 132, the instructions indicating to the healthcare worker 140 directions (e.g., backwards, forwards, up, down, left, right, and combinations thereof) in which the camera 138 is to be moved by the healthcare worker 140 prior to capturing the first image of the wound.

Figure 2:
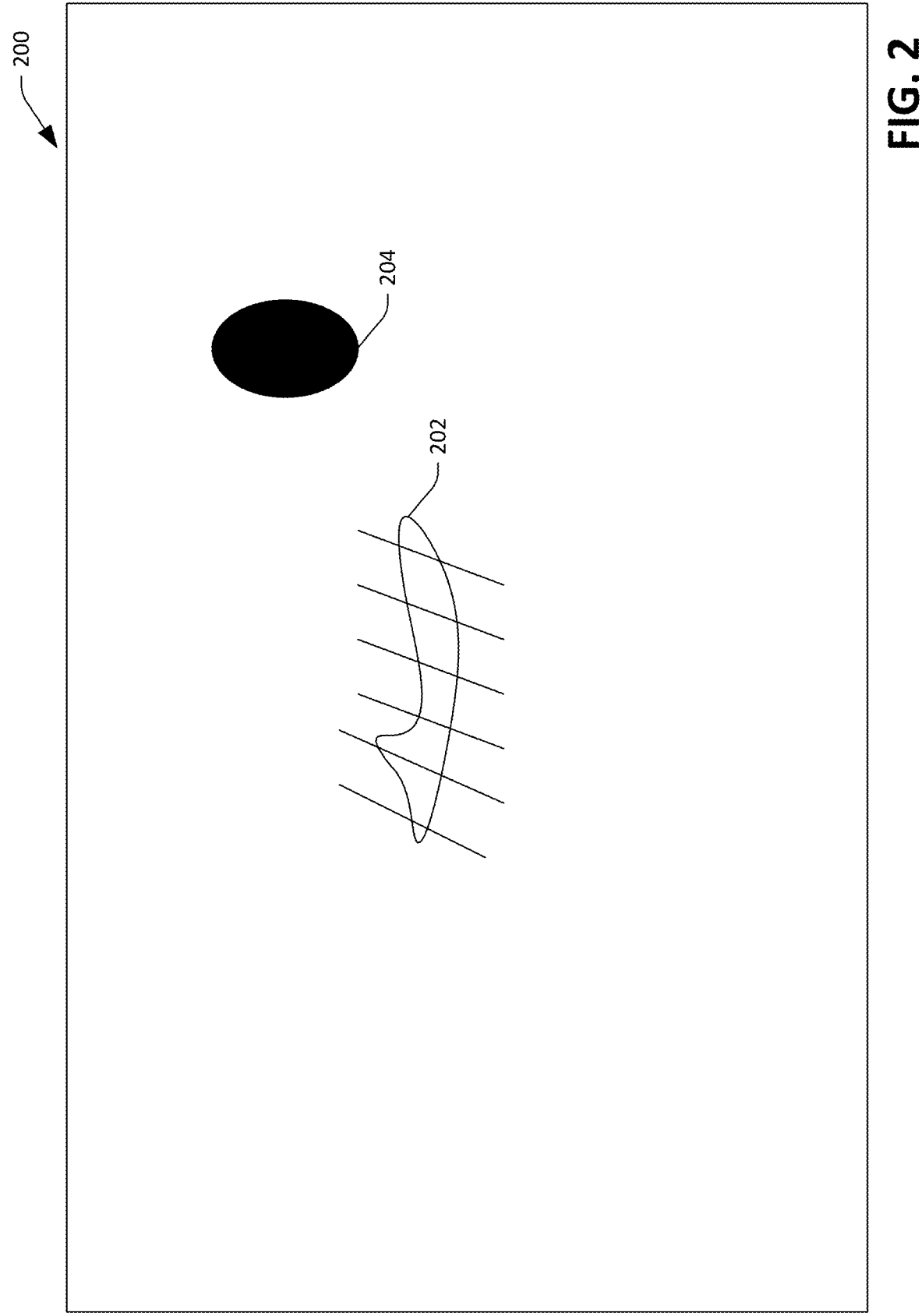
FIG. 2 illustrates an exemplary image of a wound of a patient.

Turning briefly to FIG. 2, an exemplary image 200 of a wound 202 of the patient 176 captured by the camera 138 is illustrated. In an example, the image 200 may be the first image of the wound of the patient 176 referenced above. The image 200 includes the wound 202. The wound 202 is stitched together via stiches (represented by diagonal lines in FIG. 2). The image 200 may also include a semi-permanent indicator 204 (e.g., a sticker, a temporary tattoo, etc.) that is placed on the skin of the patient 176. The client EHR 124 may utilize the semi-permanent indicator 204 in order to align the camera 138 prior to capturing the image 200 of the wound 202. Although the image 200 of the wound 202 has been described above as being captured by the camera 138, it is to be understood that the image 200 may also be captured by the camera 174 of the second computing device 156.

Turning back to FIG. 1, the client EHR 124 transmits the first image of the wound to the server EHR 108, whereupon the server EHR 108 stores the first image of the wound as part of the images 114 in the data store 110. The first image of the wound of the patient 176 may be indexed in the data store 110 by an identifier for the patient 176 received from the client EHR 124.

The client EHR 124 may also transmit camera data for the camera 138 to the server EHR 108 prior to, concurrently with, or subsequent to receiving the first image of the wound of the patient 176. The camera data is indicative of parameters of the camera 138 used by the camera 138 when capturing the first image of the wound. For instance, the parameters may include an image resolution of the camera 138 when the camera 138 captures the first image, a duration of a flash generated by the camera 138 when the camera 138 captures the first image, an intensity of the flash generated by the camera 138 when the camera 138 captures the first image, a zoom level of the camera 138 when the camera 138 captures the first image, and/or color characteristics (e.g., color temperature, white balance, etc.) of the camera 138 when the camera 138 captures the first image. Responsive to receiving the camera data for the camera 138, the server EHR 108 stores the camera data for the camera 138 in the data store 110 as part of the camera data 115 and in association with the first image of the wound of the patient 176. Similar to the first image of the wound of the patient 176, the camera data for the camera 138 may be indexed by the identifier for the patient 176.

Subsequently, it is contemplated that a period of time has passed since a time at which the first image of the wound of the patient 176 was captured by the camera 138 and that the patient 176 wishes to send a current image of the wound to the healthcare worker 140 to apprise the healthcare worker 140 of a condition of the wound. For instance, the wound of the patient 176 may be healing normally or the wound of the patient 176 may have become infected. As such, the client patient portal application 162 receives input from the patient 176 that causes the client patient portal application 162 to generate a message. The message comprises an indication that the camera 174 of the second computing device 156 is to capture a second image of the wound of the patient 176. The message may also comprise an identifier for the patient 176.

The client patient portal application 162 causes the message to be received by the server EHR 108. More specifically, the client patient portal application 162 transmits the message to the server patient portal application 148. The server patient portal application 148 transmits the message to the server EHR 108 responsive to receiving the message from the client patient portal application 162.

The server EHR 108 receives the message and generates data based upon at least the first image of the wound of the patient 176, wherein the data facilitates capturing a second image of the wound under conditions similar to conditions in which the first image of the wound was captured (described in greater detail below). The server EHR 108 may also generate the data additionally based upon the camera data for the camera 138. More specifically, responsive to receiving the message, the server EHR 108 may retrieve the first image of the wound using the identifier for the patient 176. The server EHR 108 may also retrieve the camera data for the camera 138 using the identifier for the patient 176.

Responsive to generating the data, the server EHR 108 causes the data to be received by the client patient portal application 162. More specifically, the server EHR 108 transmits the data to the server patient portal application 148. The server patient portal application 148 transmits the data to the client patient portal application 162 responsive to receiving the data from the server EHR 108.

The client patient portal application 162 receives the data from the server patient portal application 148. The data causes the client patient portal application 162 to perform actions that facilitate capturing the second image of the wound of the patient 176 under conditions similar to conditions in which the first image of the wound of the patient 176 was captured. In a first example, the data causes the client patient portal application 162 to present a semi-transparent overlay on the display 168 of the second computing device 156. The semi-transparent overlay is indicative of the first image of the wound (i.e., the semi-transparent overlay is a semi-transparent version of the first image of the wound of the patient 176). The semi-transparent overlay is overlaid upon a view of the wound shown on the display 168 as perceived through a lens of the camera 174 comprised the second computing device 156. The client patient portal application 162 captures the second image of the wound when the camera 174 is positioned with respect to the wound of the patient 176 such that at least a portion of the semi-transparent overlay is positioned over the wound shown on the display 168. Put another way, the patient 176 may move the camera 174 such that at least a portion of the semi-transparent overlay is positioned over the wound shown on the display 168.

In a second example, the data causes the client patient portal application 162 to present instructions on the display 168 of the second computing device 156. The instructions indicate one or more directions (e.g., up, down, left, right, backwards, forwards, and combinations thereof) in which the patient 176 is to move the second computing device 156 (and hence the camera 174) such that the second image of the wound is captured under similar conditions as those of the first image of the wound (i.e., an orientation of the camera 174 when capturing the second image of the wound is similar to an orientation of the camera 138 when the camera 138 captured the first image of the wound). For instance, if the camera 138 captured the first image of the wound at a first distance from the wound, the instructions may indicate that the patient 176 move the camera 174 forwards or backwards such that the second image of the wound is captured by the camera 174 of the second computing device 156 at the first distance from the wound. The client patient portal application 162 may cause the camera 174 to capture the second image of the wound of the patient 176 responsive to detecting that the patient 176 has adjusted the orientation of the camera 174 as per the instructions presented on the display 168.

In a third example, the data (which as noted above, may be based upon the camera data for the camera 138) causes the client patient portal application 162 to adjust parameters of the camera 174 to match the parameters of the camera 138 such that the camera 174 captures the second image of the wound under similar conditions to conditions in which the first image of the wound was captured. For instance, the data may cause the client patient portal application 162 to adjust a brightness of a flash of the camera 174, a duration of the flash of the camera 174, an image resolution of the camera 174, a zoom level of the camera 174, and/or a color characteristics of the camera 174 to match those of the camera 138 (or to be similar to those of the camera 138). Subsequent to adjusting the parameters of the camera 174 to match or be similar to the parameters of the camera 138 as defined in the camera data for the camera 138, the client patient portal application 162 captures the second image of the wound by way of the camera 174.

Figure 3:
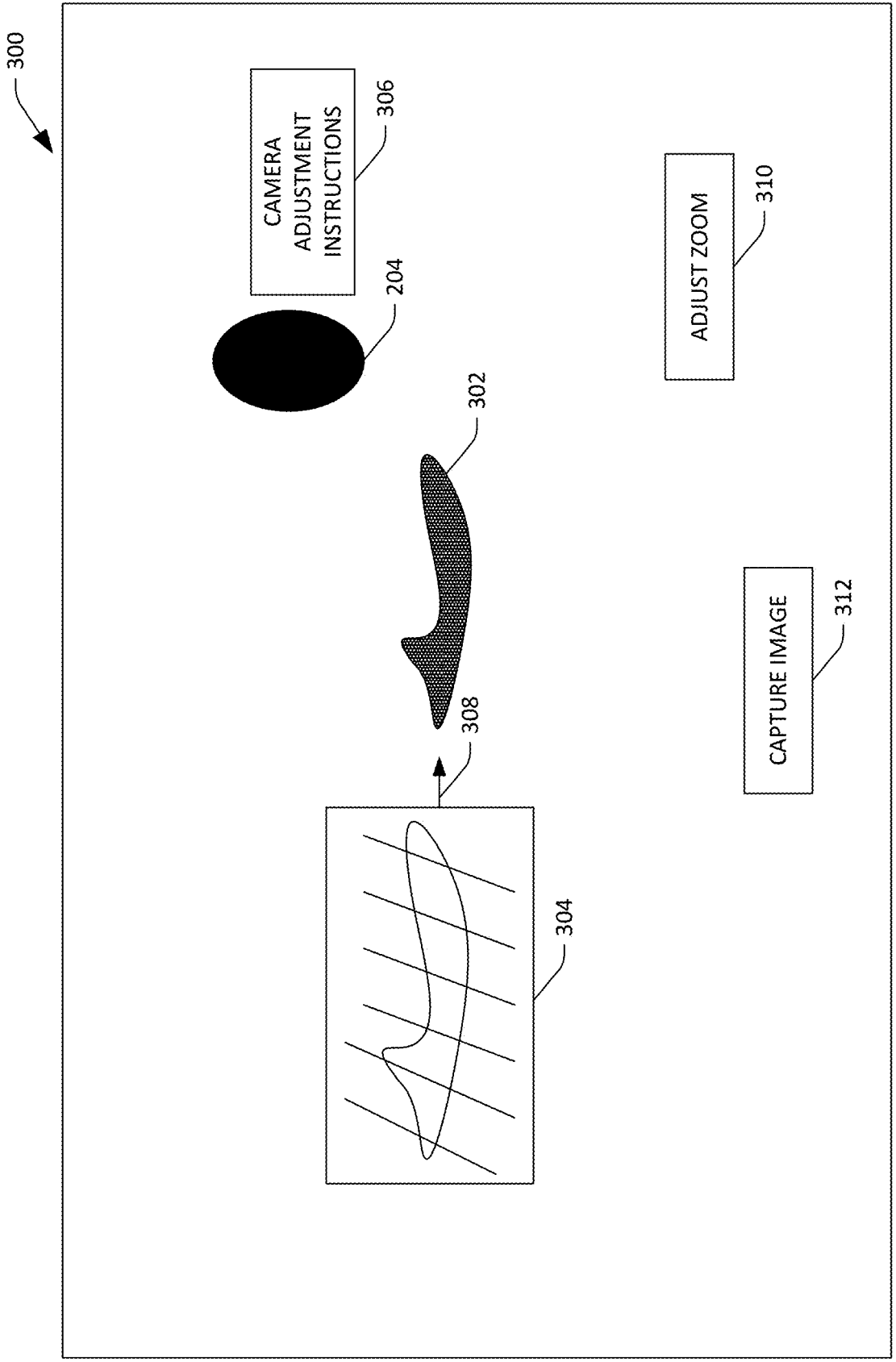
FIG. 3 illustrates a graphical user interface for capturing an image of a wound of a patient.

Turning now to FIG. 3, an exemplary GUI 300 for capturing an image of a wound of a patient is illustrated. The GUI 300 may also be referred to as a capture screen. The GUI 300 is presented on the display 168 subsequent to the client patient portal application 162 receiving the data from the server EHR 108. The GUI 300 shows a portion of the skin of the patient 176 as perceived through a lens of the camera 174 comprised by the second computing device 156. As such, the GUI 300 includes the wound 302 of the patient 176. In an example, the wound 302 may be infected (indicated by dark coloring in FIG. 3). The GUI 300 may show the semi-permanent indicator 204 and the client patient portal application 162 may utilize the semi-permanent indicator 204 to align the camera 174 prior to capturing an image of the wound 302 (e.g., the second image of the wound). The GUI 300 also includes a semi-transparent overlay 304 that is indicative of the first image of the wound (i.e., the semi-transparent overlay 304 is a semi-transparent version of the image 200 of the wound 202 described in the description of FIG. 2 above). The patient 176 may adjust an orientation of the camera 174 such that at least a portion of the semi-transparent overlay 304 is positioned over the wound 302 shown on the GUI 300.

The GUI 300 additionally includes camera adjustment instructions 306. The camera adjustment instruction 306 indicate a direction or directions in which the patient 176 is to move the camera 174 in order for the second image of the wound 302 to be captured under similar conditions as those of the first image. The GUI 300 may include a graphical indicator 308 that indicates the direction in which the second computing device 156 (and hence the camera 174) is to be moved. As shown in FIG. 3, the graphical indicator 308 indicates the patient 176 is to move the camera 174 to the right. The GUI 300 may include an adjust zoom element 310 that enables the patient 176 to adjust a zoom level of the camera 174. Furthermore, the GUI 300 includes a capture image button 312. When the GUI 300 receives a selection of the capture image button 312, the client patient portal application 162 captures an image of the wound 302 (e.g., the second image of the wound) by way of the camera 174. Although the GUI 300 has been described as being presented on the display 168 of the second computing device 156 operated by the patient 176, it is to be understood that the GUI 300 may also be presented on the display 132 of the first computing device 118 operated by the healthcare worker 140.

Turning back to FIG. 1, after the patient 176 makes any requisite adjustments to the orientation of the camera 174 and after the client patient portal application 162 makes any requisite adjustments to the parameters of the camera 174, the client patient portal application 162 captures the second image of the wound of the patient 176 by way of the camera 174. The client patient portal application 162 transmits the second image of the wound to the server patient portal application 148. The server patient portal application 148 transmits the second image of the wound to the server EHR 108 responsive to receiving the second image of the wound from the client patient portal application 162. The server EHR 108 stores the second image of the wound in the data store 110 in association with the first image of the wound of the patient 176.

It is to be understood that the images of wounds may comprise metadata. For instance, metadata for an image of a wound may include an identifier for a computing device that captured the image, an identifier for a person operating the computing device that captured the image, a date and time on which the image was captured, an identifier for a patient shown in the image, etc. Thus, the first image of the wound may comprise first metadata that identifies the patient 176 and the second image of the wound may comprise second metadata that identifies the patient 176. The server EHR 108 may remove the first metadata from the first image and the second metadata from the second image in order to de-identify the first image and the second image. The server EHR 108 may then store the first image of the wound and the second image of the wound in the data store 110 as part of a plurality of de-identified images of wounds of patients.

In an embodiment, the server EHR 108 has access to a plurality of de-identified images of wounds. The plurality of de-identified images of wounds have labels assigned thereto, wherein each label indicates whether or not a wound is infected. In the embodiment, the server EHR 108 detects that the wound of the patient 176 is infected based upon a comparison between (1) at least one of the first image of the wound of the patient 176 or the second image of the wound of the patient 176 and (2) the plurality of de-identified images of wounds. In an example, the server EHR 108 may determine a color of the wound of the patient 176 in the first image of the wound or the second image of the wound. The server EHR 108 may perform a comparison between the color and a reference color that is derived from the plurality of de-identified images of wounds. The reference color may be indicative of an infected wound. When the comparison indicates that the color is similar or identical to the reference color, the server EHR 108 may determine that the wound of the patient 176 is infected.

In an embodiment, the server EHR 108 determines a length of the wound, a width of the wound, and a depth of the wound based upon the first image of the wound of the patient 176. Responsive to determining the length of the wound, the width of the wound, and the depth of the wound, the server EHR 108 constructs a first topographical map of the wound based upon the length of the wound, the width of the wound, and the depth of the wound. The server EHR 108 may store the first topographical map of the wound in the data store 110. Subsequently, the server EHR 108 may repeat this process for the second image of the wound of the patient 176 to construct a second topographical map of the wound. The server EHR 108 may perform a comparison between the first topographical map and the second topographical map to determine whether the wound of the patient 176 is infected. For instance, if a dimension (e.g., length, width, depth) of the second topographical map is greater than a corresponding dimension of the first topographical map, the server EHR 108 may determine that the wound of the patient 176 is infected. The server EHR 108 may also determine whether the wound is infected based upon the presence or absence of other characteristics (e.g., redness, abnormal swelling, puss, etc.) of the wound as shown in either the first image of the wound or the second image of the wound.

When the server EHR 108 determines that the wound of the patient 176 is infected based upon at least one of the first image of the wound or the second image of the wound, the server EHR 108 may generate an alert and cause the alert to be transmitted to the client EHR 124 and/or the client patient portal application 162, wherein the alert indicates that the wound of the patient 176 is infected. In an example, the server EHR 108 may cause the alert to be received by the client patient portal application 162. The client patient portal application 162 may then present the alert to the patient 176 on the display 168 of the second computing device 156, wherein the alert indicates that the wound is infected and recommends that the patient 176 seek medical attention for the wound. In another example, the server EHR 108 may transmit the alert to the client EHR 124, whereupon the client EHR 124 may present the alert to the healthcare worker 140 on the display 132 of the first computing device 118.

Subsequently, it is contemplated that the healthcare wishes to view images of the wound of the patient 176 in order to ascertain how the healing of the wound of the patient 176 is progressing and/or whether the wound of the patient 176 is infected. The client EHR 124 receives input from the healthcare worker 140 that causes the client EHR 124 to transmit a request (e.g., the identifier for the patient 176) for the images of the wound to the server EHR 108. Responsive to receiving the request, the server EHR 108 retrieves the first image of the wound and the second image of the wound from the data store 110 (e.g., using the identifier for the patient 176). The server EHR 108 transmits the first image of the wound and the second image of the wound to the client EHR 124. The server EHR 108 may also transmit first metadata for the first image and second metadata for the second image to the client EHR 124.

Figure 4:
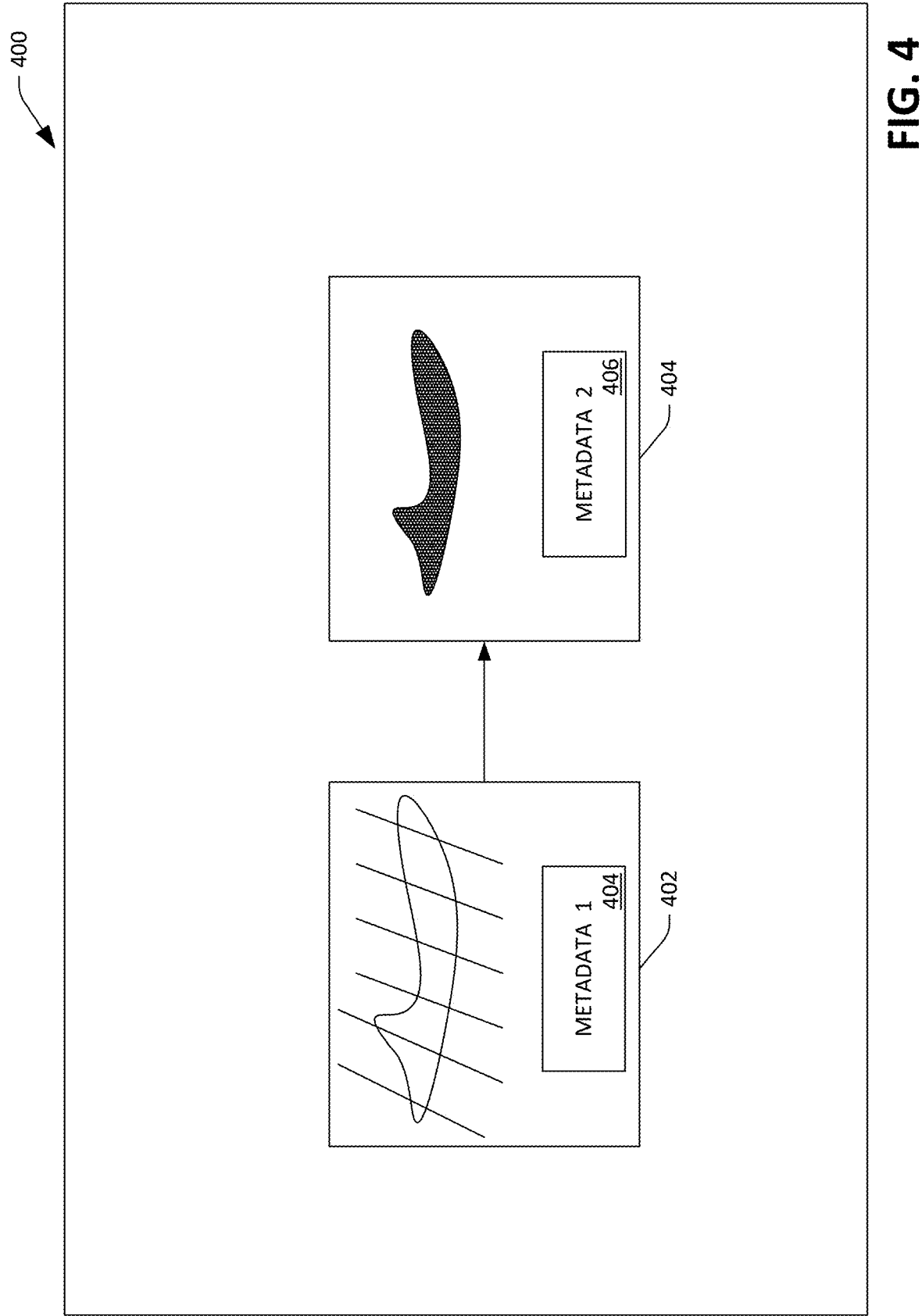
FIG. 4 illustrates a graphical user interface for presenting images of a wound of a patient.

With reference now to FIG. 4, an exemplary GUI 400 for presenting images of a wound of a patient is illustrated. Responsive to receiving the first image of the wound and the second image of the wound, the client EHR 124 may present the GUI 400 on the display 132 of the first computing device 118. The GUI 400 comprises a first image 402 of the wound and a second image of the wound 404. For instance, the first image 402 of the wound may be the image 200 and the second image of the wound may be an image that was captured using the GUI 300 described above. The GUI 400 may further display first metadata 404 for the first image 402 and second metadata 406 for the second image 404. The healthcare worker 140 may examine the images displayed on the GUI 400 in order to ascertain treatment options for the wound. For instance, if one or more of the first image or the second image indicates that the wound is infected, the healthcare worker 140 may prescribe antibiotics to the patient 176. Although the GUI 400 has been described as being presented on the display 168 of the second computing device 156 operated by the patient 176, it is to be understood that the GUI 400 may also be presented on the display 132 of the first computing device 118 operated by the healthcare worker 140.

Although the above-described technologies have been described as capturing images of wounds of patients, the above-described technologies may also be utilized to track progression of other skin markings of patients that change over time. For instance, the above-described technologies may be used to track a change of a mole of a patient over time, a change of a rash of a patient over time, etc. Moreover, although the above-described technologies have been described as capturing a first image of a wound at a first point in time and a second image of the wound at a second point in time, it is to be understood that the above-described technologies may capture many images of the wound of the patient at many different points in time.

Although the first image of the wound has been described above as being captured by the camera 138 of the first computing device 118 operated by the healthcare worker 140 and the second image of the wound has been described above as being captured by the camera 174 of the second computing device 156 operated by the patient 176, other possibilities are contemplated. For instance, the first image of the wound may be captured by the camera 174 of the second computing device 156 operated by the patient 176 and the second image of the wound may be captured by the camera 138 of the first computing device 118 operated by the healthcare worker 140. Thus, it is to be understood that the server EHR 108 may receive camera data for the camera 174 comprised by the second computing device 156, that the server EHR 108 may receive a message generated by the client EHR 124 executing on the first computing device 118, that the server EHR 108 may cause the data (described above) to be transmitted to the client EHR 124, and so forth. Additionally, both the first image of the wound and the second image of the wound may be captured by the same computing device (e.g., the first computing device 118 operated by the healthcare worker 140 or the second computing device 156 operated by the patient 176).

In an embodiment, the server patient portal application 148 may perform some or all of the functionality described above as being executed by the server EHR 108. For instance, in the embodiment, the server patient portal application 148 may receive the first image of the wound of the patient 176 and the second image of the wound of the patient 176, store the first image of the wound and the second image of the wound in the data store 150, receive a message generated by the client EHR 124 or the client patient portal application 162, generate the data that facilitates capturing images of the wound of the patient 176 under similar conditions, and so forth.

Figure 5:
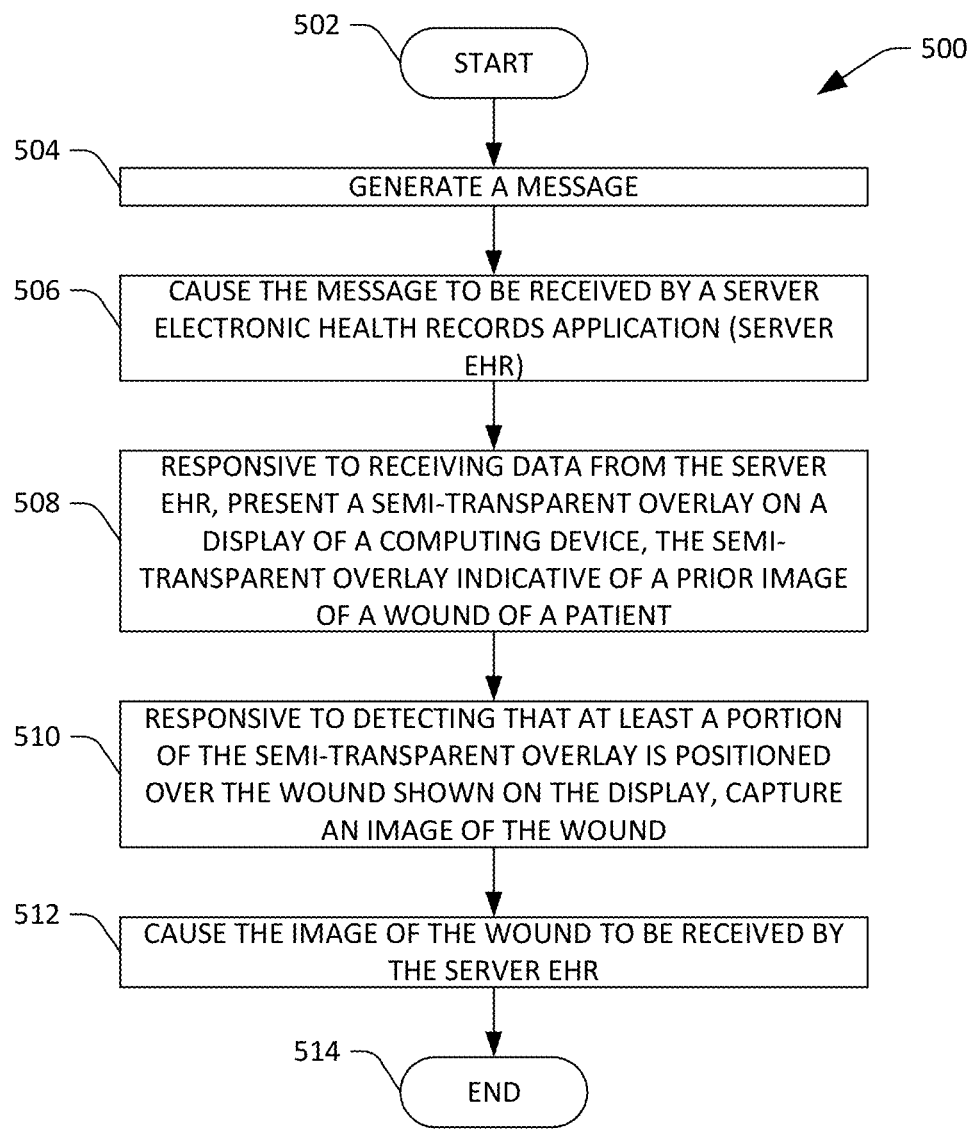
FIG. 5 is a flow diagram that illustrates an exemplary methodology performed by a computing device that facilitates wound tracking for a patient.
Figure 6:
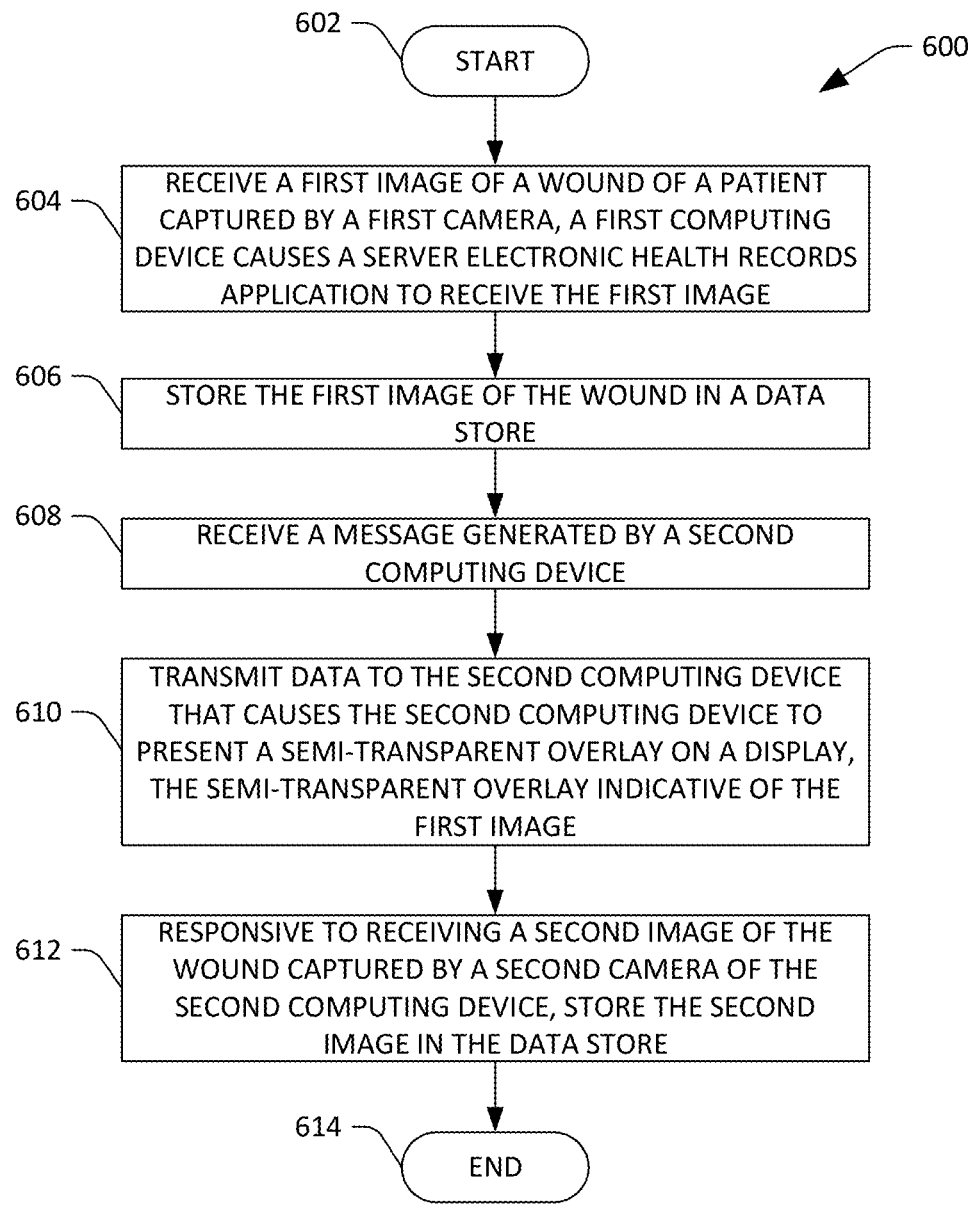
FIG. 6 is a flow diagram that illustrates an exemplary methodology performed by a server computing device that facilitates wound tracking for a patient.
Figure 7:
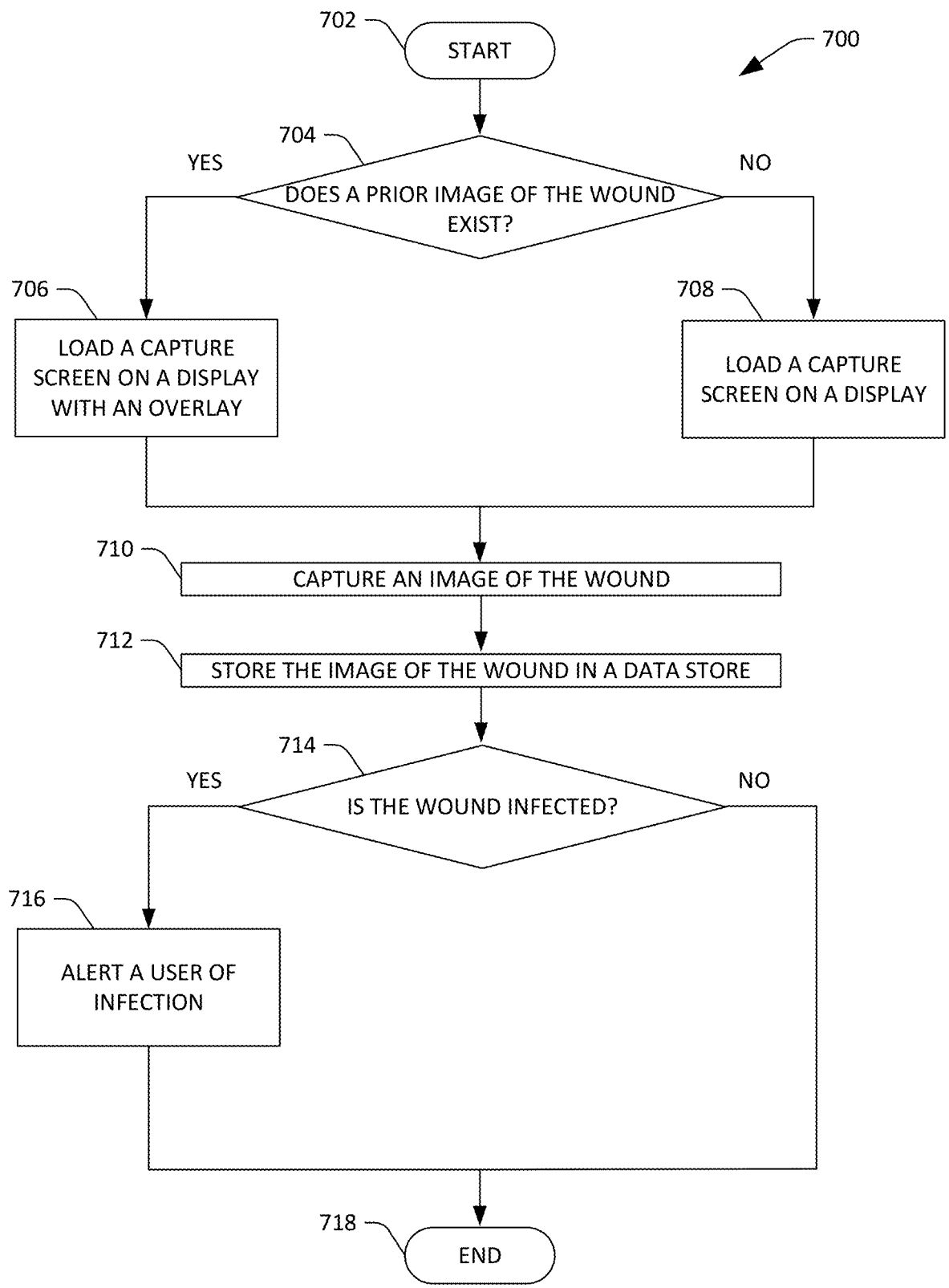
FIG. 7 is a flow diagram that illustrates an exemplary methodology performed by a computing device that facilitates wound tracking for a patient.

FIGS. 5-7 illustrate exemplary methodologies relating to wound tracking for a patient. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 performed by a computing device that facilitates wound tracking for a patient is illustrated. The methodology 500 begins at 502, and at 504, the computing device receives input from a user (e.g., a healthcare worker, a patient) of the computing device that causes the computing device to generate a message. The message comprises an identifier for the patient and an indication that the computing device is to capture an image of a wound of the patient by way of a camera comprised by the computing device. At 506, the computing device causes the message to be received by a server EHR executing on a server computing device. The server EHR accesses a prior image of the wound of the patient based upon the identifier for the patient and generates data based in part upon the prior image of the wound. At 508, responsive to receiving the data from the server EHR, the computing device presents a semi-transparent overlay on a display of the computing device. The semi-transparent overlay is indicative of the prior image of the wound and is overlaid upon a view of the wound shown on the display as perceived through a lens of the camera. Subsequently, at 510, responsive to detecting that at least a portion of the semi-transparent overlay is positioned over the wound shown on the display, the computing device captures the image of the wound via the camera. At 512, the computing device causes the image of the wound to be received by the server EHR, wherein the server EHR stores the image of the wound in a data store in association with the prior image of the wound. The methodology 500 concludes at 514.

Turning now to FIG. 6, a methodology 600 performed by a server EHR executing on a server computing device that facilitates wound tracking for a patient is illustrated. The methodology 600 begins at 602, and at 604, the server EHR receives a first image of a wound of a patient captured by a first camera. A first computing device causes the first image to be received by the server EHR. At 606, the server EHR stores the first image of the wound in a data store accessible to the server EHR. At 608, subsequent to storing the first image of the wound in the data store, the server EHR receives a message generated a second computing device. The message comprises an indication that the second computing device is to capture a second image of the wound of the patient.

At 610, responsive to receiving the message, the server EHR causes data to be transmitted to the second computing device, the data based in part upon the first image of the wound. The data causes the second computing device to present a semi-transparent overlay on a display of the second computing device. The semi-transparent overlay is indicative of the first image of the wound and is overlaid upon a view of the wound shown on the display as perceived through a lens of a second camera comprised by the second computing device. The second computing device captures the second image of the wound by way of the second camera when the second camera is positioned with respect to the wound such that at least a portion of the semi-transparent overlay is positioned over the wound shown on the display. The second computing device then causes the second image to be received by the server EHR. At 612, responsive to receiving the second image of the wound, the server EHR stores the second image of the wound in the data store. The methodology 600 concludes at 614.

With reference now to FIG. 7, a methodology 700 performed by a computing device that facilitates wound tracking for a patient is illustrated. The methodology 700 begins at 702, and at 704 the computing device determines whether a prior image of a wound of the patient exists (i.e., determines whether the prior image of the wound is stored in a data store) by communicating with a server computing device that executes an EHR that has access to images of wounds of patients stored in the data store. When the prior image of the wound exists (i.e., the prior image is stored in the data store), at 706, the computing device loads a capture screen (i.e., a GUI) on a display of the computing device along with a semi-transparent overlay that is indicative of the prior image of the wound, the semi-transparent overlay being overlaid with a view of the wound as perceived through a lens of a camera comprised by the computing device. When the prior image of the wound does not exist (i.e., the prior image is not stored in the data store), at 708, the computing devices loads the capture screen on the display without the semi-transparent overlay. When the prior image of the wound does not exist, the server computing device may transmit an indication to the computing device that the prior image of the wound is not stored in the data store.

At 710, the computing device captures an image of the wound of the patient via a camera of the computing device. At 712, the computing device causes the image of the wound to be stored in a data store. At 714, the computing device communicates with the server computing device to determine whether the wound of the patient is infected. When the wound is infected, at 716, the computing device alerts a user (e.g., the patient, a healthcare worker, etc.) of the infection. When the wound is not infected, the computing device does not alert the user. The methodology 700 concludes at 718.

Figure 8:
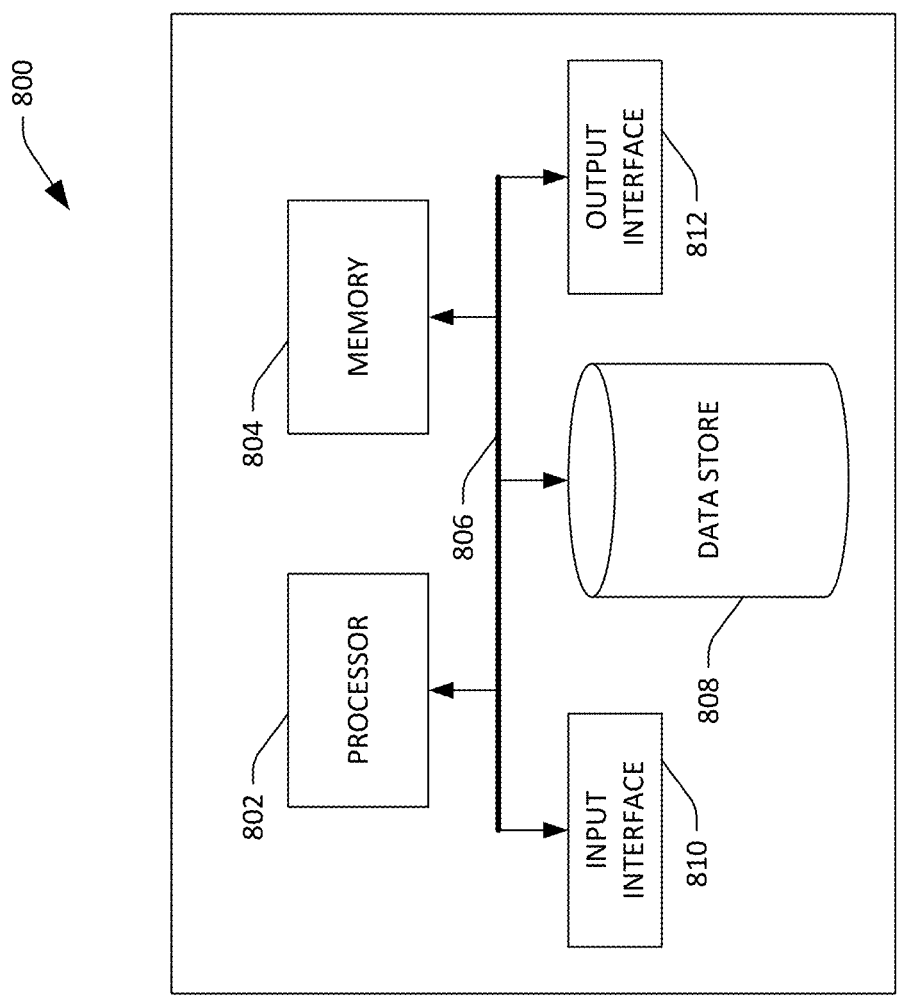
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that captures an image of a wound of a patient. By way of another example, the computing device 800 can be used in a system that stores images of a wound of a patient. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store clinical data, images of wounds of patients, camera data for cameras that capture the images of the wounds, etc.

The computing device 800 additionally includes a data store 808 that is accessible by the processor 802 by way of the system bus 806. The data store 808 may include executable instructions, clinical data, images of wounds of patients, camera data for cameras that capture the images of the wounds, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device, comprising: a processor; and
memory storing a server electronic health records application (server EHR) that, when executed by the processor, causes the processor to perform acts comprising:

receiving, from a client electronic health records application (client EHR) executing on a client computing device that is in network communication with the server computing device, an identifier for a patient that is being treated at a point of care by a healthcare worker operating the client computing device;

determining whether a prior image of a wound of the patient exists in a data store based upon the identifier for the patient;

when the prior image of the wound exists in the data store:
  transmitting first data to the client EHR, wherein the first data causes a semitransparent overlay to be presented on a first display of the client computing device, wherein the semi-transparent overlay is indicative of the prior image of the wound, wherein the semi-transparent overlay is overlaid upon a first view of the wound shown on the first display of the client computing device as perceived through a first lens of a first camera of the client computing device, wherein a first image of the wound of the patient is captured by the first camera when the first camera is positioned with respect to the wound such that at least a portion of the semi-transparent overlay is positioned over the wound shown on the first display while the patient is present at the point of care;
  receiving the first image from the client EHR; and
  storing the first image of the wound in the data store; and when the prior image of the wound does not exist in the data store:
  transmitting an indication to the client EHR that the prior image of the wound does not exist in the data store, wherein the first camera captures the first image of the wound of the patient subsequent to the client EHR receiving the indication and while the patient is present at the point of care;
  receiving the first image of the wound from the client EHR;
  storing the first image of the wound in the data store;
  subsequent to storing the first image of the wound, receiving, from a server patient portal application executing on a second server computing device that is in network communication with the server computing device, a message that originates from a client patient portal application executing on a patient computing device operated by the patient that is in network communication with the second server computing device, wherein the message comprises the identifier for the patient;
  upon determining that the first image of the wound is stored in the data store based upon the identifier for the patient, transmitting second data to the server patient portal application, wherein the second data is forwarded to the client patient portal application by the server patient portal application, wherein the second data causes the semi-transparent overlay to be presented on a second display of the patient computing device, wherein the semi-transparent overlay is overlaid upon a second view of the wound shown on the second display as perceived through a second lens of the second camera, wherein the second image of the wound is captured by the second camera when the second camera is positioned with respect to the wound such that at least the portion of the semi-transparent overlay is positioned over the wound shown on the second display, wherein the second image of the wound is transmitted from the client patient portal application to the server patient portal application; and
  responsive to receiving the second image of the wound from the server patient portal application, storing the second image of the wound in the data store.

2. The server computing device of claim 1, the acts further comprising:
  detecting that the wound of the patient is infected based upon a comparison between:
    at least one of the first image of the wound or the second image of the wound;
    and a plurality of images of wounds; and
  when the comparison indicates that the wound is infected, transmitting an alert to at least one of the client computing device or the patient computing device, the alert indicating that the wound is infected, wherein at least one of the client computing device or the patient computing device presents the alert.

3. The server computing device of claim 1, the acts further comprising:
  responsive to receiving a request for images of the wound from the patient computing device, causing the first image of the wound and the second image of the wound to be transmitted to the patient computing device, wherein the first image of the wound and the second image of the wound are presented on the second display of the patient computing device.

4. The server computing device of claim 1, the acts further comprising:
  when the prior image of the wound does not exist in the data store:
    receiving first parameters of the first camera when the first camera captured the first image of the wound; and
    storing the first parameters of the first camera in association with the first image in the data store, wherein the second data is further based upon the first parameters of the first camera, wherein the second data further causes second parameters of the second camera to be adjusted to match the first parameters of the first camera prior to the second image of the wound being captured by the second camera.

5. The server computing device of claim 4, wherein the first parameters of the first camera include at least one of:
  an image resolution of the first camera;
  a duration of a flash generated by the first camera;
  an intensity of the flash generated by the first camera;
  a zoom level of the first camera; or
  color characteristics of the first camera.

6. The server computing device of claim 1, the acts further comprising: determining a length of the wound based upon the first image of the wound; determining a width of the wound based upon the first image of the wound; determining a depth of the wound based upon the first image of the wound; and
  constructing a topographical map of the wound based upon the length, the width, and the depth.

7. The server computing device of claim 1, wherein when the prior image of the wound exists in the data store, the first data causes first guidance to be presented on the first display of the client computing device, the first guidance indicating a first direction in which the healthcare worker is to move the first camera prior to the first camera capturing the first image of the wound, wherein when the prior image of the wound does not exist in the data store, the second data causes second guidance to be presented on the second display of the patient computing device, the second guidance indicating a second direction in which the patient is to move the second camera prior to the second camera capturing the second image of the wound.

8. The server computing device of claim 1, wherein the first image of the wound comprises first metadata that identifies the patient, wherein the second image of the wound comprises second metadata that identifies the patient, the acts further comprising:
removing the first metadata from the first image;
removing the second metadata from the second image; and
storing the first image and the second image in the data store as part of a plurality of de-identified images of wounds.

9. A method executed by a processor of a server computing device while the processor executes a server electronic health records application (server EHR), the method comprising:
receiving, from a client electronic health records application (client EHR) executing on a client computing device that is in network communication with the server computing device, an identifier for a patient that is being treated at a point of care by a healthcare worker operating the client computing device;
determining whether a prior image of a wound of the patient exists in a data store based upon the identifier for the patient;
when the prior image of the wound exists in the data store:
transmitting first data to the client EHR, wherein the first data causes a semi-transparent overlay to be presented on a first display of the client computing device, wherein the semi-transparent overlay is indicative of the prior image of the wound, wherein the semitransparent overlay is overlaid upon a first view of the wound shown on the first display of the client computing device as perceived through a first lens of a first camera of the client computing device, wherein a first image of the wound of the patient is captured by the first camera when the first camera is positioned with respect to the wound such that at least a portion of the semi-transparent overlay is positioned over the wound shown on the first display while the patient is present at the point of care;
receiving the first image of the wound from the client EHR; and
storing the first image of the wound in the data store; and
when the prior image of the wound does not exist in the data store:
transmitting an indication to the client EHR that the prior image of the wound does not exist in the data store, wherein the first camera captures the first image of the wound of the patient subsequent to the client EHR receiving the indication and while the patient is present at the point of care;
storing the first image of the wound in the data store;
subsequent to storing the first image of the wound in the data store, receiving, from a server patient portal application executing on a second server computing device that is in network communication with the server computing device, a message that originates from a client patient portal application executing on a patient computing device operated by the patient that is in network communication with the second server computing device, wherein the message comprises the identifier for the patient;
upon determining that the first image of the wound is stored in the data store based upon the identifier for the patient, transmitting second data to the server patient portal application, wherein the second data is forwarded to the client patient portal application by the server patient portal application, wherein the second data causes the semi-transparent overlay to be presented on a second display of the patient computing device, wherein the semi-transparent overlay is overlaid upon a second view of the wound shown on the second display as perceived through a second lens of the second camera, wherein the second image of the wound is captured by the second camera when the second camera is positioned with respect to the wound such that at least the portion of the semi-transparent overlay is positioned over the wound shown on the second display, wherein the second image of the wound is transmitted from the client patient portal application to the server patient portal application; and
responsive to receiving the second image of the wound from the server patient portal application, storing the second image of the wound in the data store.

10. The method of claim 9, further comprising:
determining a color of the wound based upon at least one of the first image or the second image;
performing a comparison between the color and a reference color that is indicative of an infection; and
when the comparison indicates that the wound is infected, causing an alert to be transmitted to the client EHR, the alert indicating that the wound is infected, wherein the alert is presented on the first display of the client computing device.

11. The method of claim 9, further comprising:
when the prior image of the wound exists in the data store:
receiving parameters of a camera that captured the prior image of the wound; and
storing the parameters of the camera in association with the prior image in the data store, wherein the first data is further based upon the parameters of the camera, wherein the first data further causes first parameters of the first camera to be adjusted to match the parameters of the camera prior to the first camera capturing the first image of the wound.

12. The method of claim 9, wherein the client computing device and the patient computing device are mobile computing devices.

13. The method of claim 9, further comprising:
responsive to receiving a request for images of the wound from the client computing device, causing the first image of the wound and the second image of the wound to be transmitted to the client EHR, wherein the first image of the wound and the second image of the wound are presented within a GUI of the client EHR shown on the first display.

14. The method of claim 13, wherein the first image of the wound presented within the GUI is labeled with first metadata for the first image, wherein the second image of the wound presented within the GUI is labeled with second metadata for the second image.

15. A computer-readable storage medium comprising a server electronic health records application (server EHR)

that, when executed by a processor of a server computing device, causes the processor to perform acts comprising:
  receiving, from a server patient portal application executing on a second server computing device that is in network communication with the server computing device, an identifier for a patient;
  determining whether a prior image of a wound of the patient exists in a data store based upon the identifier for the patient;
  when the prior image of the wound exists in the data store:
    transmitting first data to the server patient portal application, wherein the first data is forwarded to a client patient portal application executing on a patient computing device operated by the patient that is in network communication with the second server computing device, wherein the first data causes a semi-transparent overlay to be presented on a first display of the patient computing device, wherein the semi-transparent overlay is indicative of the prior image of the wound, wherein the semi-transparent overlay is overlaid upon a first view of the wound shown on the first display of the patient computing device as perceived through a first lens of a first camera of the patient computing device, wherein a first image of the wound of the patient is captured by the first camera when the first camera is positioned with respect to the wound such that at least a portion of the semi-transparent overlay is positioned over the wound shown on the first display, wherein the first image of the wound is transmitted from the client patient portal application to the server patient portal application;
    receiving the first image of the wound from the server patient portal application; and
    storing the first image of the wound in the data store; and
  when the prior image of the wound does not exist in the data store:
    transmitting an indication to the server patient portal application that the prior image of the wound does not exist in the data store, wherein the server patient portal application forwards the indication to the client patient portal application, wherein the first camera captures the first image of the wound of the patient subsequent to the indication being forwarded, wherein the client patient portal application transmits the first image of the wound to the server patient portal application;
    receiving the first image of the wound from the server patient portal application; storing the first image of the wound in the data store;
    subsequent to storing the first image of the wound in the data store, receiving, from a client electronic health records application (client EHR) executing on a client computing device operated by a healthcare worker that is in network communication with the server computing device, a message comprising the identifier for the patient, wherein the patient is at a point of care with the healthcare worker;
    upon determining that the first image of the wound is stored in the data store based upon the identifier for the patient, transmitting second data to the client EHR, wherein the second data causes the semi-transparent overlay to be presented on a second display of the client computing device, wherein the semi-transparent overlay is overlaid upon a second view of the wound shown on the second display as perceived through a second lens of a second camera of the client computing device, wherein the second image of the wound is captured by the second camera when the second camera is positioned with respect to the wound such that at least the portion of the semi-transparent overlay is positioned over the wound shown on the second display; and
    responsive to receiving the second image of the wound from the client EHR, storing the second image of the wound in the data store.

16. The computer-readable storage medium of claim 15, wherein when the prior image of the wound exists in the data store, the first data causes first guidance to be presented on the first display of the patient computing device, the first guidance indicating a first direction in which the patient is to move the first camera prior to the first camera capturing the first image of the wound, wherein when the prior image of the wound does not exist in the data store, the second data further causes second guidance to be presented on the second display of the client computing device, the second guidance indicating a second direction in which the healthcare worker is to move the second camera prior to the second camera capturing the second image of the wound.

17. The computer-readable storage medium of claim 15, the acts further comprising:
  determining that the wound is infected based upon at least one of the first image of the wound or the second image of the wound; and
  responsive to determining that the wound is infected, causing an alert to be transmitted to the client EHR, the alert indicating that the wound is infected, wherein the alert is presented to the healthcare worker on the second display of the client computing device.

18. The server computing device of claim 1, wherein the patient computing device is a mobile computing device operated by the patient.

* * * * *